US006596877B2

(12) United States Patent
Shieh et al.

(10) Patent No.: US 6,596,877 B2
(45) Date of Patent: Jul. 22, 2003

(54) ACCELERATED PROCESS FOR PREPARING O-METHYL PHENOLS, N-METHYL HETEROAROMATIC COMPOUNDS, AND METHYLATED AMINOPHENOLS

(75) Inventors: Wen-Chung Shieh, Berkeley Heights, NJ (US); Steven Dell, Madison, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/982,147

(22) Filed: Oct. 17, 2001

(65) Prior Publication Data

US 2003/0073848 A1 Apr. 17, 2003

(51) Int. Cl.$^7$ ...................... C07D 233/58; C07C 211/00
(52) U.S. Cl. ..................................... 548/343.5; 564/305
(58) Field of Search ........................ 564/305; 548/343.5

(56) References Cited

U.S. PATENT DOCUMENTS

| 4,192,949 A | * | 3/1980 | Merger et al. |
| 4,513,146 A | | 4/1985 | Thompson ................. 560/231 |
| 5,387,718 A | * | 2/1995 | Köhler et al. |
| 5,453,516 A | * | 9/1995 | Fischer et al. |

FOREIGN PATENT DOCUMENTS

EP   0104598 A1 *   4/1984

OTHER PUBLICATIONS

Campbell et al, Microwave Accelerated Preparation of Aryl 2–(N,N–diethylamino)ethyl Ethers, 1994, Bioorganic and Medicinal Chemistry Letters, 4(21) pp. 2627–2630.*
Tundo, P., "Selective monomethylation reactions of methylene–active compounds with dimethylcarbonate. An example of clean synthesis", Pure Appl. Chem., vol. 72, No. 9, pp. 1793–1797 (2000).
Basak et al., "Chemoselective O–Methylation of Phenols under Non–aqueous Condition", Tetrahedron Lett., vol. 39, pp. 4883–4886 (1998).
Voskresensky et al., "Selective One–Pot N–Monomethylation of 2–Nitroanilines under PTC Conditions", Syn. Comm., vol. 30, No. 19, pp. 3523–3526 (2000).
Lissel et al., "Dimethylcarbonat als Methylierungsmittel unter Phasen–Transfer–Katalytischen Bedingungen", Synthesis, pp. 382–383 (1986).
Barcelo et al., "Penaalkylguanidines as Etherification and Esterification Catalysts", Tetrahedron, vol. 46, No. 6, pp. 1839–1848 (1990).
Selva et al., "Selective Mono–N–Methylation of Primary Aromatic Amines by Dimethyl Carbonate over Faujasite X– and Y–type Zeolites", J. Chem. Soc., Perkin Trans. 1, pp. 1041–1045 (1997).
Selva et al., "Reaction of Primary Aromatic Amines with Alkyl Carbonates over NaY Faujasite: A Convenient and Selective Access to Mono–N–alkyl Anilines", J. Org. Chem., vol. 66, No. 3, pp. 677–680 (2001).
Perosa et al., "Alkyl Methyl Carbonates as Methylating Agents. The O–Methylation of Phenols.", SynLett, Nos. 1 and 2, pp. 272–274 (2000).
Lee et al., "Convenient O–Methylation of Phenols with Dimethyl Carbonate", SynLett, pp. 1063–1064 (1998).
Kanie et al., "A Facile Synthesis of Trifluoromethylamines by Oxidative Desulfurization–Fluorination of Dithiocarbamates", Bull. Chem. Soc. Jpn., vol. 71, No. 8, pp. 1973–1991 (1998).
Ahmad et al., "Preparation of 3–Substituted 6,7–Dimethoxyquinoxalin–2(1H)–ones and Studies of Their Potential as Fluoroionophores", Tetrahedron, vol. 51, No. 47, pp. 12899–12910 (1995).
Johnstone et al., "A Rapid, Simple, and Mild Procedure for Alkylation of Phenols, Alcohols, Amides and Acids", Tetrahedron, vol. 35, pp. 2169–2173 (1979).
"CRC Handbook of Chemistry and Physics", (D.R.Lind, Ed.), 75$^{th}$ Edition, CRC Press, Inc., pp. 8–45–8–55 (1994).
Granitza et al., "Efficient Acylation of Hydroxy Functions by Means of Fmoc Amino Acid Fluorides", J. Chem. Soc., Chem. Commun., pp. 2223–2224 (1995).

* cited by examiner

*Primary Examiner*—Johann Richter
*Assistant Examiner*—Paul A. Zucker
(74) *Attorney, Agent, or Firm*—John D. Thallemer

(57) ABSTRACT

An accelerated process for preparing an O-methyl phenol comprising reacting a phenol with dimethyl carbonate in the presence of a catalyst selected from 1,8-diazabicyclo[5.4.0] undec-7-ene; 1,4-diazabicyclo[2.2.2]octane; and dimethylaminopyridine. According to another aspect, the invention provides an accelerated process for preparing an N-methyl heteroaromatic compound comprising reacting an NH-containing heteroaromatic compound with dimethyl carbonate in the presence of a catalyst selected from 1,8-diazabicyclo[5.4.0]undec-7-ene; 1,4-diazabicyclo[2.2.2] octane; and dimethylaminopyridine. According to an additional aspect, the invention provides an accelerated process for preparing a methylated aminophenol comprising reacting an aminophenol having at least one N—H with dimethyl carbonate in the presence of a catalyst selected from 1,8-diazabicyclo[5.4.0]undec-7-ene; 1,4-diazabicyclo[2.2.2] octane; and dimethylaminopyridine. The process of the invention is especially advantageous since the process: (1) utilizes an environmentally friendly methylating reagent, dimethylcarbonate; (2) produces a high yield of the O-methyl phenols, N-methyl aromatic amines, and/or methylated aminophenols, generally 97–100% conversion; and (3) does not require a high-pressure (autoclave) reactor.

13 Claims, No Drawings

US 6,596,877 B2

ACCELERATED PROCESS FOR PREPARING O-METHYL PHENOLS, N-METHYL HETEROAROMATIC COMPOUNDS, AND METHYLATED AMINOPHENOLS

FIELD OF THE INVENTION

The present invention provides an accelerated process for preparing a O-methyl phenol (anisole), N-methyl heteroaromatic compound, or a methyl aminophenol, comprising reacting a phenol, an NH-containing heteroaromatic compound, or an aminophenol having at least one N—H, with dimethyl carbonate in the presence of a catalyst selected from 1,8-diazabicyclo[5.4.0]undec-7-ene (DBU); 1,4-diazabicyclo[2.2.2]octane (DABCO); and dimethylaminopyridine (DMAP).

BACKGROUND OF THE INVENTION

Methylation of alcohols and amines is an important process in chemistry. However, due to the environmental and human impact of using toxic and unsafe methylating reagents such as methyl iodide or dimethyl sulfate, the investigation of safer, generally applicable alternatives continues. As an alternative to these toxic methylating agents, dimethyl carbonate (DMC) has attracted considerable attention for the methylation of phenols, anilines, and activated methylenes. DMC is non-toxic and generates $CO_2$ and methanol as by-products during methylations. DMC is also a volatile liquid with a boiling point of 90° C. Hence, the unreacted DMC can be easily recovered by distillation from the reaction mixture and reused. Furthermore, DMC has been shown to be quite selective in monomethylation of primary aromatic amines and C-methylation of arylacetonitriles and arylacetoesters.

U.S. Pat. No. 4,513,146 describes a method for producing esters from highly hindered carboxylic acids and carbonates. The method involves reacting the highly hindered carboxylic acid with a carbonate with or without a catalyst at a temperature of 175° C. according to the examples. U.S. Pat. No. 4,513,146 states that exemplary cataysts are nitrogen-containing heterocyclic catalysts such as pyridine, 4-(dimethylamino)pyridine, imidazole, 2,6-lutidine, and 2,4,6-collidine.

Shimizu, I; Lee, Y., *Synlett*, pg. 1063 (1998) discloses methylation of 1-naphthol with DMC using $Na_2CO_3$ which required 168 hours at 120° C. for 91% completion. Lissel, M.; Schmidt, S.; Neumann, B., *Synthesis*, pg. 382 (1986) discloses N-methylation of benzimidazole with DMC using $K_2CO_3$ 18-crown-6, which required 8 hours at 100° C. for 81% yield.

Therefore, it would be advantageous from a production standpoint to develop a more efficient process which utilizes dimethyl carbonate as a reactant in the production of O-methyl phenols, N-methyl heteroaromatic compounds, and methyl aminophenols.

SUMMARY OF THE INVENTION

The invention provides an accelerated process for preparing an O-methyl phenol (anisole) comprising reacting a phenol with dimethyl carbonate in the presence of a catalyst selected from the group consisting of 1,8-diazabicyclo[5.4.0]undec-7-ene; 1,4-diazabicyclo[2.2.2]octane; dimethylaminopyridine; and combinations thereof.

According to another aspect, the invention provides an accelerated process for preparing an N-methyl heteroaromatic compound comprising reacting an NH-containing heteroaromatic compound with dimethyl carbonate in the presence of a catalyst selected from the group consisting of 1,8-diazabicyclo[5.4.0]undec-7-ene; 1,4-diazabicyclo[2.2.2]octane; dimethylaminopyridine; and combinations thereof.

According to another aspect, the invention provides an accelerated process for preparing a methylated aminophenol comprising reacting an aminophenol having at least one N—H with dimethyl carbonate in the presence of a catalyst selected from the group consisting of 1,8-diazabicyclo[5.4.0]undec-7-ene 1,4-diazabicyclo[2.2.2]octane; dimethylaminopyridine; and combinations thereof.

The process of the invention is especially advantageous for preparing O-methyl phenols, N-methyl heteroaromatic compounds, and methyl aminophenols, since the process: (1) utilizes an environmentally friendly methylating reagent, dimethylcarbonate; (2) produces a high yield of the O-methyl phenols, N-methyl heteroaromatic compounds, and methylated aminophenols, generally 97–100% conversion; and (3) does not require a high-pressure (autoclave) reactor.

DESCRIPTION OF THE INVENTION

The process of the invention is used to prepare an O-methyl phenol and/or an N-methyl heteroaromatic compound, and/or a methylated aminophenol, depending on the choice of reactant. In one embodiment of the invention, the process involves reacting a phenol with dimethyl carbonate to form an O-methyl phenol. As used herein, "phenol" refers to a reactant and "O-methyl phenol" refers to the product. The phenol may be unsubstituted or substituted with one or more substituent groups or combinations of substituent groups. In addition, the substituent groups attached to the phenol may be combined together with carbon atoms on the phenol to form a 5 to 7 membered aromatic or hetero aromatic ring. Suitable substituent groups on the phenol are groups which do not preclude formation of the O-methyl phenol. Examples of substituent groups on the phenol include, but are not limited to, alkyl, alkenyl, aryl, (cycloalkyl)alkyl, arylalkyl, cycloalkyl, and halogen. Such substituent groups may be unsubstituted or contain groups such as mercapto, hydroxyl, amino, selenyl or carboxyl. When an aryl group or a group containing an aryl portion is used as a substituent group, it may be homocyclic or heterocyclic, and it may comprise a single ring or it may comprise a ring assembly.

Preferred phenols include the following:

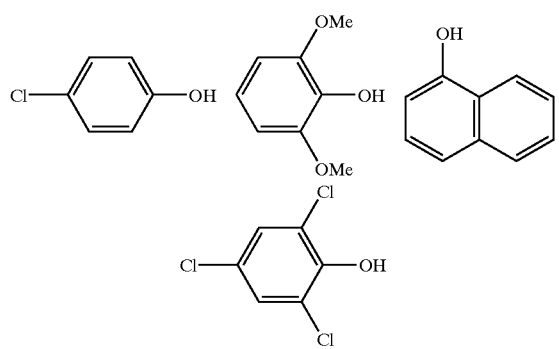

In another embodiment of the invention, the process involves reacting an NH-containing heteroaromatic compound with dimethyl carbonate to form an N-methyl heteroaromatic compound. As used herein, "NH-containing heteroaromatic compound" refers to a reactant having at least one aromatic group and at least one N—H attached to the aromatic group, and "N-methyl heteroaromatic compound" refers to the product. The NH-containing heteroaromatic compound may be unsubstituted or substituted with one or more substituent groups or combinations of substituent groups. In addition, the substituent groups attached to the NH-containing heteroaromatic compound may be combined together with carbon atoms on the NH-containing heteroaromatic compound to form a 5 to 7 membered aromatic or heteroaromatic ring. Suitable substituent groups on the NH-containing heteroaromatic compound are groups which do not preclude formation of the N-methyl heteroaromatic compound. Examples of substituent groups on the NH-containing heteroaromatic compound include, but are not limited to, alkyl, alkenyl, aryl, (cycloalkyl)alkyl, arylalkyl, cycloalkyl, and halogen. Such substituent groups may be unsubstituted or contain groups such as mercapto, hydroxyl, amino, selenyl or carboxyl. When an aryl group or a group containing an aryl portion is used as a substituent group, it may be homocyclic or heterocyclic, and it may comprise a single ring or it may comprise a ring assembly.

Preferred NH-containing heteroaromatic compounds include the following:

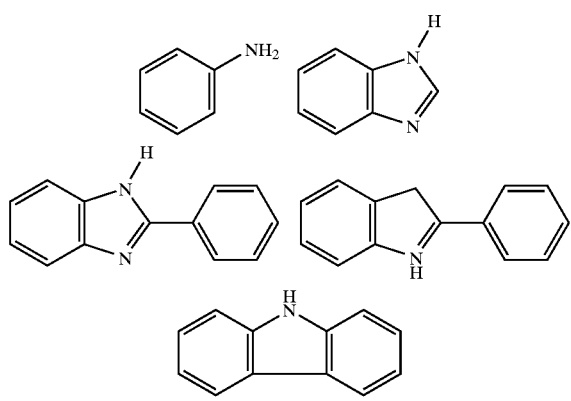

In another embodiment of the invention, the process involves reacting an aminophenol having at least one N—H with dimethyl carbonate to form a methylated aminophenol. As used herein, "aminophenol having at least one N—H" refers to a reactant having a phenol group and at least one N—H directly attached to the aromatic ring of the phenol group, and "methylated aminophenol" refers to the product which contains at least one methoxy or N—CH$_3$ group. The aminophenol having at least one N—H may be unsubstituted or substituted with one or more substituent groups or combinations of substituent groups. In addition, the substituent groups attached to the aminophenol having at least one N—H may be combined together with carbon atoms on the aromatic ring of the phenol group to form a 5 to 7 membered aromatic or hetero aromatic ring. Suitable substituent groups on the aminophenol having at least one N—H are groups which do not preclude formation of the methylated aminophenol. Examples of substituent groups on the methylated aminophenol include, but are not limited to, alkyl, alkenyl, aryl, (cycloalkyl)alkyl, arylalkyl, cycloalkyl, and halogen. Such substituent groups may be unsubstituted or contain groups such as mercapto, hydroxyl, amino, selenyl or carboxyl. When an aryl group or a group containing an aryl portion is used as a substituent group, it may be homocyclic or heterocyclic, and it may comprise a single ring or it may comprise a ring assembly. A preferred aminophenol having at least one N—H is m-aminophenol.

The phenol, NH-containing heteroaromatic compound, or aminophenol having at least one N—H, as described above, are reacted with dimethyl carbonate. Dimethyl carbonate has formula (I)

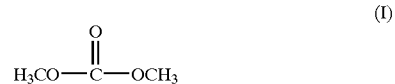

(I)

The reaction of the phenol, NH-containing heteroaromatic compound, or aminophenol having at least one N—H with dimethyl carbonate is conducted in the presence of a catalyst which is selected from 1,8-diazabicyclo[5.4.0]undec-7-ene (DBU); 1,4-diazabicyclo[2.2.2]octane (DABCO); and dimethylaminopyridine (DMAP). A combination of catalysts may also be used.

The equivalent ratio of the catalyst to the phenol, NH-containing heteroaromatic compound, or aminophenol having at least one N—H, as initially present, is in the range of from about 0.1:1 to about 2:1. More preferably, the equivalent ratio of the catalyst to the phenol, NH-containing heteroaromatic compound, or aminophenol is from about 0.5:1 to about 1:1, most preferably about 1:1.

Preferably, the process of the invention is conducted at a temperature of from about 10° C. to about 300° C. More preferably, the process is conducted at a temperature of from about 80° C. to 200° C.; and most preferably from about 90° C. to about 160° C. In one embodiment of the invention, microwave irradiation is used to provide the desired reaction temperature. The process is conducted preferably under a pressure of from about 1 atm to about 100 atm, more preferably, from 1 atm to 50 atm. Most preferably, the process is conducted under a pressure of 1 atm.

The process of the invention is preferably conducted in the liquid phase. It may be carried out batchwise, continuously, semibatchwise or semicontinuously. Dimethyl carbonate is generally a liquid under the conditions of the reaction and it may act as a solvent for the phenol, NH-containing heteroaromatic compound, or aminophenol having at least one N—H. Typically, but not necessarily, excess dimethyl carbonate is employed relative to the amount of phenol, NH-containing heteroaromatic compound, or aminophenol having at least one N—H. Although extrinsic solvent is not ordinarily employed, it may be used when desired or when necessary to dissolve one or more of the reactants. Examples of suitable extrinsic solvents include: acetonitrile, ethyl acetate, acetone, benzene, toluene, dioxane, dimethylformamide and chlorinated solvents such as chloroform, methylene chloride, ethylene chloride, carbon tetrachloride and chlorobenzene. A combination of solvents may also be used. Preferably, the process is conducted without an extrinsic solvent.

Optionally, the process of the invention may include one or more amine bases. Preferred amine bases are trialkylamines and ethylenediamines. Specific amine bases include, but are not limited to, triethylamine, N,N-diisopropylethylamine and N,N'-diisopropylethylenediamine. A combination of amine bases may also be used. A preferred amount of amine base is about 1:1 equivalent based on the amount of phenol, NH-containing heteroaromatic compound, or aminophenol having at least one N—H.

Following preparation, the product of the process, O-methyl phenol, N-methyl heteroaromatic compound, and/ or methylated aminophenol may be recovered from the reaction mixture by any of the various techniques known to the art. Distillation at reduced pressure is a preferred technique.

The following nonlimiting examples illustrate further aspects of the invention.

EXAMPLE 1

Preparation of Trimethoxybenzene Using DBU

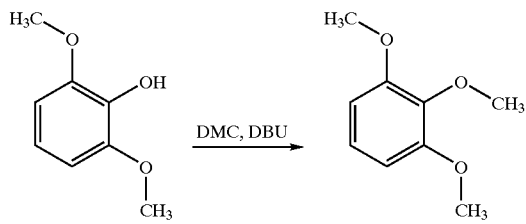

To a solution of 2,6-dimethoxyphenol (1.0 g, 6.49 mmol) in DMC (10 mL), 1,8-diazabicyclo[5.4.0]undec-7-ene (DBU)(0.99 g, 6.49 mmol) was added and the resulting solution was heated to reflux (90° C.) for 4.5 hours. The reaction was cooled to ambient temperature and diluted with EtOAc (50 mL) and $H_2O$ (40 mL). The organic layer was separated and washed in sequence with $H_2O$ (40 mL), 2M HCl (2×40 mL), 2M NaOH (2×40 mL) and $H_2O$. The organic layer was dried over $Na_2SO_4$, filtered and concentrated under vacuum to give trimethoxybenzene as a solid. The yield of trimethoxybenzene as deteremined by HPLC was 99%.

EXAMPLE 2

Preparation of Trimethoxybenzene Using Dabco™

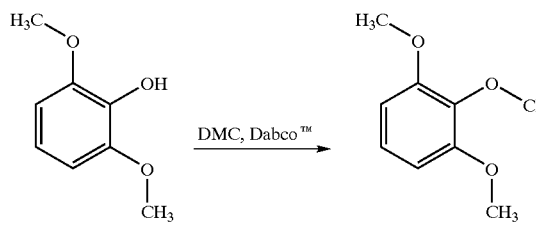

To a solution of 2,6-dimethoxyphenol (1.03 g, 6.68 mmol) in DMC (10 mL), Dabco™ (0.75 g, 6.68 mmol) was added and the resulting mixture was heated to reflux (90° C.) for 2 hours. The yield of trimethoxybenzene as determined by HPLC was 99%.

EXAMPLE 3

Preparation of Trimethoxybenzene Using DMAP

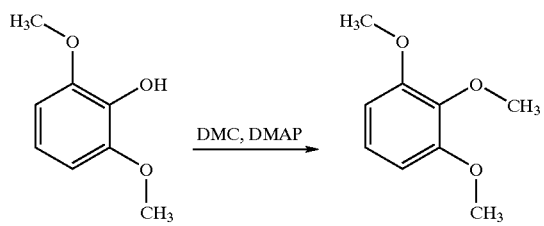

To a solution of 2,6-dimethoxyphenol (1.02 g, 6.62 mmol) in DMC (10 mL), DMAP (0.81 g, 6.62 mmol) was added and the resulting mixture was heated to reflux (90° C.) for 4 hours. The yield of trimethoxybenzene as determined by HPLC was 99%.

EXAMPLE 4

Preparation of 1-Methyl-2-Phenylbenzimidazole Using DBU

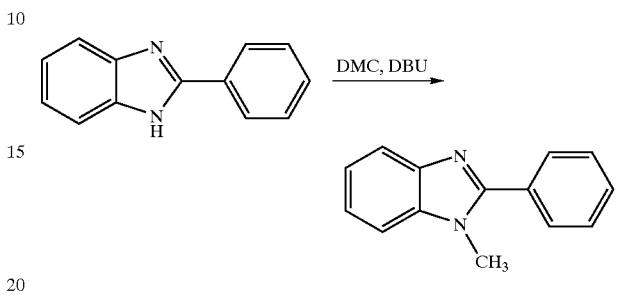

To a mixture of 2-phenylbenzimidazole (1.02 g, 5.25 mmol) in DMC (10 mL), DBU (0.80 g, 5.25 mmol) was added and the resulting mixture was heated to reflux (90° C.) for 6 hours. The solvent was evaporated under vacuum and the resulting oil was dissolved in methylene chloride (2 mL) and filtered through silica gel (2:1 EtOA/hexane). The solvent was evaporated under vacuum to afford 1-methyl-2-phenylbenzimidazole as a solid. The yield of 1-methyl-2-phenylbenzimidazole as determined by HPLC analysis was 98%.

EXAMPLE 5

Preparation of 1-methyl-2-phenylbenzimidazole Using Dabco™

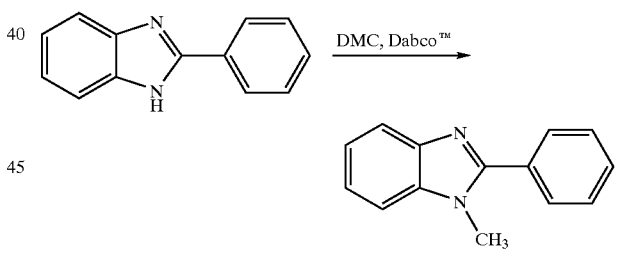

To a mixture of 2-phenylbenzimidazole (2.02 g, 10.4 mmol) in DMC (10 mL), Dabco™ (1.17 g, 10.4 mmol) was added and the resulting mixture was heated to reflux (90° C.) for 3 hours. The yield of 1-methyl-2-phenylbenzimidazole as determined by HPLC analysis was 99%.

EXAMPLE 6

Preparation of 1-Methyl-2-phenylbenzimidazole Using DMAP

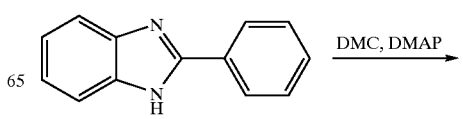

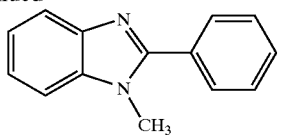

To a mixture of 2-phenylbenzimidazole (2.02 g, 10.4 mmol) in DMC (10 mL) and DMF (5 mL), DMAP (1.27 g, 10.4 mmol) was added and the resulting mixture was heated to reflux (90° C.) for 4 hours. The yield of 1-methyl-2-phenylbenzimidazole as determined by HPLC analysis was 99%.

EXAMPLE 7

Preparation of 1-methoxynaphthalene Using 1 Equivalent of DBU

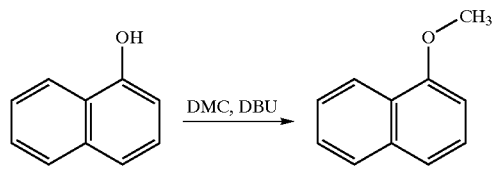

To a solution of 1-naphthol (1.0 g, 6.94 mmol) in DMC (10 mL), DBU (1.06 g, 6.94 mmol) was added and the resulting mixture was heated to reflux (90° C.) for 16 hours. The reaction was cooled to ambient temperature and diluted with EtOAc (50 mL) and $H_2O$ (40 mL). The organic layer was separated and washed in sequence with 2M HCl (2×40 mL), 2M NaOH (2×40 mL) and $H_2O$. The organic layer was dried over $Na_2SO_4$, filtered and concentrated under vacuum to give 1-methoxynaphthalene as an oil. The yield of 1-methoxynaphthalene as determined by HPLC was 99% conversion.

EXAMPLE 8

Preparation of 1-methoxynaphthalene Using 0.5 Equivalent of DBU.

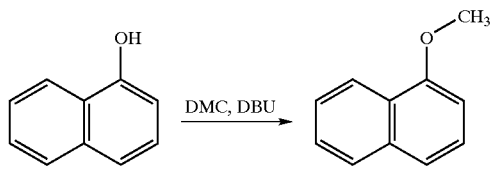

To a solution of 1-naphthol (1.0 g, 6.94 mmol) in DMC (10 mL) and DMF (1.6 mL), DBU (0.53 g, 3.47 mmol) was added and the resulting mixture was heated to reflux (90° C.) for 120 hours. HPLC analysis indicated a 99% conversion to 1-methoxynaphthalene.

The results in Examples 7 shows that a 1:1 equivalent of DBU to substituted phenol (1-naphthol) produced 99% conversion to 1-methoxynaphthalene in 16 hours; however, 0.5:1 equivalent of DBU to reactant in Example 8 took 120 hours to achieve 99% conversion to 1-methoxynaphthalene.

EXAMPLE 9 (COMPARISON)

Preparation of 1-methoxynaphthalene Using No Base

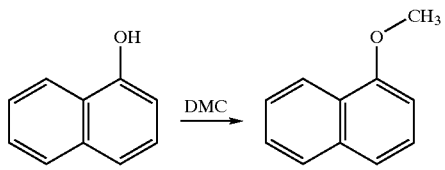

1-Naphthol (1.0 g, 6.94 mmol) was dissolved in DMC (10 mL) and the solution was heated to reflux (90° C.) for 24 hours. HPLC analysis indicated that no product (1-methoxynaphthalene) had been formed.

EXAMPLE 10

Preparation of Trimethoxybenzene Using DBU and Microwave Heating.

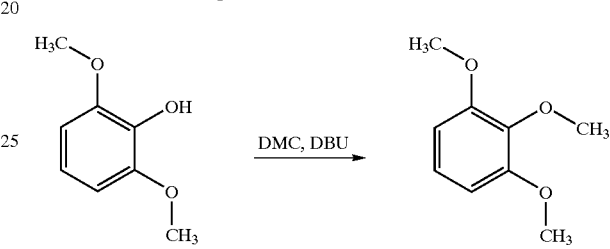

A solution of 2,6-dimethoxyphenol (5.0 g, 32.1 mmol) in DMC (50 mL), 1,8-diazabicyclo[5.4.0]undec-7-ene (DBU) (4.9 g, 32.1 mmol), and acetonitrile (50 mL), was passed through a Milestone ETHOS-CFR continuous-flow reactor preheated to 160° C. at 20 bar. The reaction products were analyzed by HPLC after each pass (6 min). The yield of trimethoxybenzene after 12 minutes as determined by HPLC was 97%.

The results in Example 10 show that the relative rate of reaction was about 25 times faster to achieve essentially the same conversion using microwave heating at 160° C., as compared to using thermal heating to prepare trimethoxybenzene in Example 1 which was conducted at 90° C.

EXAMPLE 11

Preparation of 1-Methyl-2-Phenylbenzimidazole Using DBU and Microwave Heating.

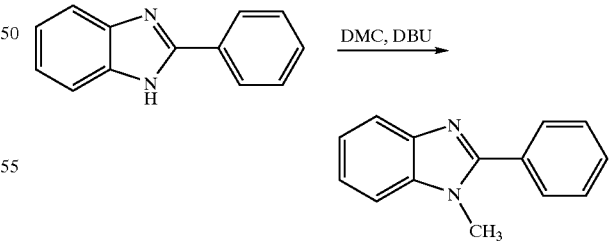

A solution of 2-phenylbenzimidazole (5 g, 25.7 mmmol) in DMC (50 mL), 1,8-diazabicyclo[5.4.0]undec-7-ene (DBU) (3.9 g, 25.7 mmol), and acetonitrile (50 mL), was passed through a Milestone ETHOS-CFR continuous-flow reactor preheated to 160° C. at 20 bar. The reaction products were analyzed by HPLC after each pass (6 min). The yield of 1-methyl-2-phenylbenzimidazole after 12 minutes as determined by HPLC was 97%.

The results in Example 11 show that the relative rate of reaction was about 30 times faster to achieve essentially the same conversion using microwave heating at 160° C., as compared to using thermal heating to prepare 1-methyl-2-phenylbenzimidazole in Example 4 which was conducted at 90° C.

EXAMPLE 12

Preparation of 1-methoxynaphthalene Using 1 Equivalent of DBU and Microwave Heating.

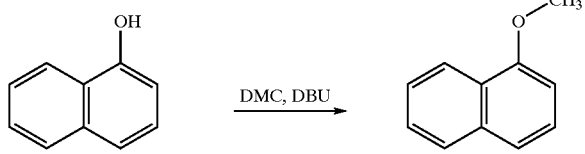

A solution of 1-naphthol (5 g, 34.7 mmmol) in DMC (50 mL), 1,8-diazabicyclo[5.4.0]undec-7-ene (DBU) (5.3 g, 34.7 mmol), and dimethylformamide (50 mL), was passed through a Milestone ETHOS-CFR continuous-flow reactor preheated to 160° C. at 20 bar. The reaction products were analyzed by HPLC after each pass (6 min). The yield of 1-methoxynaphthalene after 12 minutes as determined by HPLC was 99%.

The results in Example 12 show that the relative rate of reaction was about 80 times faster to achieve essentially the same conversion using microwave heating at 160° C., as compared to using thermal heating to prepare 1-methoxynaphthalene in Example 7 which was conducted at 90° C.

The process of the invention is especially advantageous for preparing O-methyl phenols, N-methyl heteroaromatic compounds, and methylated aminophenols, since the process: (1) utilizes an environmentally friendly methylating reagent, dimethylcarbonate; (2) produces a high yield of the O-methyl phenols, N-methyl heteroaromatic compounds, and methylated aminophenols, generally 97–100% conversion; and (3) does not require a high-pressure (autoclave) reactor.

While the invention has been described with particular reference to certain embodiments thereof, it will be understood that changes and modifications may be made by those of ordinary skill within the scope and spirit of the following claims:

What is claimed is:

1. An accelerated process for preparing an N-methyl heteroaromatic compound comprising reacting an NH-containing heteroaromatic compound with dimethyl carbonate in the presence of a catalyst selected from the group consisting of 1,8-diazabicyclo[5.4.0]undec-7-ene; 1,4-diazabicyclo[2.2.2]octane; dimethylaminopyridine; and combinations thereof.

2. The process according to claim 1 wherein the NH-containing heteroaromatic compound is substituted with one or more substituent groups.

3. The process according to claim 2 wherein at least two adjacent carbon atoms on the NH-containing heteroaromatic compound form a 5 to 7 membered aromatic or heteroaromatic ring.

4. The process according to claim 2 wherein a substituent group on the NH-containing heteroaromatic compound is selected from the group consisting of alkyl, alkenyl, aryl, (cycloalkyl)alkyl, arylalkyl, cycloalkyl, and halogen.

5. The process according to claim 4 wherein the substituent group on the NH-containing heteroaromatic compound is substituted with a group selected from the group consisting of mercapto, hydroxyl, amino, selenyl and carboxyl.

6. The process according to claim 1 wherein the molar ratio of the catalyst to the NH-containing heteroaromatic compound is in the range of from about 0.1:1 to about 2:1.

7. The process according to claim 6 wherein the molar ratio of the catalyst to the containing heteroaromatic compound is in the range of from about 0.5:1 to about 1:1.

8. The process according to claim 7 wherein the molar ratio of the catalyst to the NH-containing heteroaromatic compound is about 1:1.

9. The process according to claim 1 wherein the catalyst is 1,8-diazabicyclo[5.4.0]undec-7-ene.

10. The process according to claim 1 wherein the process is conducted at a temperature of from about 10° C. to about 300° C.

11. The process according to claim 10 wherein the temperature is from about 80° C. to about 200° C.

12. The process according to claim 11 wherein the temperature is from about 90° C. to about 160° C.

13. The process according to claim 10 wherein the temperature is achieved by microwave irradiation.

* * * * *

UNITED STATES PATENT AND TRADEMARK OFFICE
CERTIFICATE OF CORRECTION

PATENT NO.    : 6,596,877 B2
DATED         : July 22, 2003
INVENTOR(S)   : Shieh et al.

It is certified that error appears in the above-identified patent and that said Letters Patent is hereby corrected as shown below:

<u>Column 10,</u>
Line 29, should read as follows: -- ratio of the catalyst to the NH-containing heteroaromatic com- --.

Signed and Sealed this

Fourth Day of May, 2004

JON W. DUDAS
*Acting Director of the United States Patent and Trademark Office*